United States Patent [19]

Gergely et al.

[11] Patent Number: 5,409,712
[45] Date of Patent: Apr. 25, 1995

[54] MODIFIED STARCH AND PROCESS FOR ITS PREPARATION

[75] Inventors: Gerhard Gergely; Irmgard Gergely; Thomas Gergely, all of Vienna, Austria

[73] Assignee: Gergely & Co., Vienna, Austria

[21] Appl. No.: 612,919

[22] Filed: Nov. 13, 1990

[30] Foreign Application Priority Data

Nov. 14, 1989 [CH] Switzerland .................. 4099/89

[51] Int. Cl.$^6$ .................. A61K 9/16; A61K 9/18
[52] U.S. Cl. .................. 424/499; 424/465
[58] Field of Search .......... 424/456, 499, 465, 462, 424/466, 468; 106/210; 514/866

[56] References Cited

U.S. PATENT DOCUMENTS

| 4,508,740 | 4/1985 | McSweeney | 426/250 |
| 4,551,177 | 11/1985 | Trubiano | 106/210 |
| 4,578,264 | 3/1986 | Stricker | 424/456 |
| 4,863,724 | 9/1989 | Schepky | 514/866 |
| 4,898,736 | 2/1990 | Katdare | 424/465 |
| 4,911,930 | 3/1990 | Gergely | 424/490 |
| 4,983,399 | 1/1991 | Maish | 424/465 |
| 5,051,262 | 9/1991 | Panoz et al. | 424/468 |
| 5,064,656 | 11/1991 | Gergely | 424/464 |

FOREIGN PATENT DOCUMENTS 0250267  6/1987 European Pat. Off.
0366621 10/1989 European Pat. Off.

*Primary Examiner*—Thurman K. Page
*Assistant Examiner*—William E. Benston, Jr
*Attorney, Agent, or Firm*—Ostrolenk, Faber, Gerb & Soffen

[57] ABSTRACT

Starch as a tablet excipient, in particular a disintegrant, is laden with one to twenty, in particular with three to ten, % by weight of physiologically safe compound which is soluble in a solvent which does not swell the starch. Edible organic acids, such as, for example, citric acid, 1-tartaric acid, adipic acid or fumaric acid, as well as polyvinylpyrrolidone—in particular relatively long-chain, straight-chain polyvinylpyrrolidone—are particularly suitable for this purpose.

10 Claims, No Drawings

MODIFIED STARCH AND PROCESS FOR ITS PREPARATION

In the pharmaceutical industry, there is an increasing need for tablet excipients. Particularly since the conventional excipients, such as lactose (owing to signs of intolerance), mannitol, xylitol, etc., are increasingly being rejected because of laxative effects, it is necessary to develop tablet excipients which do not allow criticism of their pharmacological properties.

An ideal tablet excipient would be starch, which is physiologically safe.

The possibilities of using starch in tablet formulations are limited since starch as such is difficult to compress directly because, owing to its structure, it has no binding capabilities. To achieve the desired compressibility, it would be necessary to granulate starch or starch-containing products. In the main, aqueous solutions of dextrin, gum arabic, polyvinylpyrrolidone and other binders have been used for this purpose to date.

However, starch can be used, according to the invention, as a tablet excipient if the starch is laden with substances which are dissolved in solvents which cannot hydrolyze starch.

For example, organic acids or water soluble polymers such as polyvinylpyrrolidones, having relatively long chains are suitable for imparting binding properties to starch. With these binding properties, the disintegrant character of the starch is largely retained; it is merely the amount of the lead which determines the extent to which the starch is still swellable and capable of disintegration or whether it can be used only as a tablet excipient without disintegration.

It is of course also possible to use such modified starches in combination with other disintegrants, such as, for example, crosslinked polyvinylpolypyrrolidone, so that the starch can be used either as a disintegrant or only as a tablet excipient.

Regarding the swellability of disintegrants, the article by A. H. Bronnsack in *Pharm. Ind.* 38, 12, 1181-1185 (1976) gives, particularly in the introduction, a good overview, which is herewith incorporated by reference in the present description.

If it is now desired —for whatever reasons —to produce tablets to which a relatively large amount of starch (regardless of origin) has been added, lower tablet hardnesses result owing to the poor compression properties.

According to the invention, this can be improved by the measures described herein. Advantageous further embodiments of the invention, in particular a process for the preparation of the starch modified according to the invention, are also described.

For example, the starch is treated with an acid in alcoholic solution. If 10 parts of tartaric acid in 30 parts of alcohol are added to 100 parts of rice starch, the tartaric acid crystallizes inside the starch after evaporation of the alcohol and imparts substantially improved compression properties to the starch. Since, owing to the addition of alcohol, the starch cannot swell but its water content even decreases from an original water content of 12-15% to 6-7% on drying, this step is particularly suitable for compressing even difficult formulations to give hard tablets.

Such starch treatments using different substances can be carried out in normal granulators; it is particularly advantageous, however, to evacuate the starch at temperatures of 40°-50° C., to suck the alcoholic solution into the starch, with the result that the solution can even penetrate partially into the cell structure of the starch grains, and to carry out subsequent evaporation of the solvent in vacuo. In this manner, various substances can be excellently anchored inside the starch grains.

If the vacuum loading of starches is used, it is even possible to incorporate alcoholic polymer solutions, e.g. PVP solutions in the starch to improve the compression properties, and relatively long-chain PVP (K 90) is of course particularly suitable.

EXAMPLE 1

500 parts of starch are heated to 40° C. in a mixing vessel, and a solution of 100 parts of alcohol and 50 parts of citric acid is added. The solution is then dried to a moisture content of 6% in a tray drier or fluidized-bed drier.

In this case too, it is true that, when used for starch loading, the freely soluble citric acid gives harder tablets but a dissolution time which is 3 to 4 times longer if the starch is to be used as a disintegrant in an disintegrating effervescent tablet. Other substances are therefore preferable, such as those below.

EXAMPLE 2

A solution of 130 parts of alcohol and 50 parts of adipic acid are sucked into 500 parts of starch in vacuo at 40° C., distributed and then dried at 40°-50° C. in vacuo.

Here too, the water content of the starch decreases from the original value of 12% to 7%. This laden starch is particularly suitable for disintegrating effervescent tablets since the adipic acid is more poorly water-soluble.

EXAMPLES 3 and 4

500 parts of starch are laden with a solution of 100 parts of alcohol and 40 parts of tartaric acid or with 150 parts of alcohol and 20 parts of fumaric acid, as under Example 1.

EXAMPLE 5

A solution of 100 ml of alcohol and 5 g of PVP K 90 is added to 500 parts of starch. This starch too gives good tablet hardnesses and does not increase the disintegration or dissolution time.

In principle, a very wide range of substances are suitable for the modification, provided that they are soluble in organic solvents, mainly alcohol, and have poor water-solubility.

We claim:

1. A tablet excipient, useful as a disintegrant, which is starch containing therein one to twenty percent by weight of a physiologically safe excipient compound which is soluble in an alcoholic solvent, said compound being selected from the group consisting of edible organic acids and polyvinylpyrrolidone, said compound being distributed over or penetrated into the starch grains.

2. Starch as claimed in claim 1, containing three to ten % by weight of said compound.

3. Starch as claimed in claim 1, wherein said compound is the edible organic acid.

4. Starch as claimed in claim 1, wherein said compound is the polyvinylpyrrolidone.

5. A process for the preparation of a tablet excipient useful as a disintegrant, said process comprising heating starch in a vacuum mixing vessel to 40°-50° C. sucking an alcoholic solution of a physiologically safe excipient compound selected from the group consisting of edible organic acids and polyvinylpyrrolidones in an alcoholic solvent into the starch, thereby distributing said compound over or penetrating said compound into the starch grains, and then drying the starch treated in this manner.

6. Starch as claimed in claim 3, containing three to ten % by weight of the acid.

7. Starch as claimed in claim 6, wherein the acid is selected from the group consisting of citric acid, 1-tartaric acid, adipic acid and fumaric acid.

8. Starch as claimed in claim 3, wherein the acid is selected from the group consisting of citric acid, 1-tartaric acid, adipic acid and fumaric acid.

9. Starch as claimed in claim 4, wherein the polyvinylpyrrolidone is relatively long-chained, straight chain polyvinylpyrrolidone.

10. A tablet excipient useful as a disintegrant, produced by the process comprising heating starch in a vacuum mixing vessel to 40°–50° C., sucking an alcoholic solution of a physiologically safe excipient compound selected from the group consisting of edible organic acids and polyvinylpyrrolidone in an alcoholic solvent into the starch, thereby distributing said compound over or penetrating said compound into the starch grains and then drying the starch treated in this manner.

* * * * *